United States Patent [19]
Morrison

[11] Patent Number: 5,300,252
[45] Date of Patent: Apr. 5, 1994

[54] ETHER FREE ORGANOMETALLIC AMIDE COMPOSITIONS

[75] Inventor: Robert C. Morrison, Gastonia, N.C.

[73] Assignee: FMC Corporation, Philadelphia, Pa.

[21] Appl. No.: 927,689

[22] Filed: Aug. 7, 1992

Related U.S. Application Data

[60] Division of Ser. No. 496,556, Mar. 19, 1990, abandoned, which is a division of Ser. No. 160,229, Feb. 25, 1988, Pat. No. 4,944,894, and a continuation-in-part of Ser. No. 25,412, Mar. 13, 1987, abandoned.

[51] Int. Cl.$^5$ .............................................. C09K 3/00
[52] U.S. Cl. .............................. 252/182.3; 252/182.12
[58] Field of Search ...................... 252/182.12, 182.3

[56] References Cited

U.S. PATENT DOCUMENTS

| | | | |
|---|---|---|---|
| 3,742,077 | 6/1973 | Kamienski et al. | 260/668 B |
| 3,822,219 | 7/1974 | Kamienski et al. | 252/431 |
| 3,847,883 | 11/1974 | Kamienski et al. | 260/83.7 |
| 4,467,108 | 8/1984 | Gigliotti et al. | 560/180 |
| 4,499,292 | 2/1985 | Sprague et al. | 549/459 |
| 4,668,794 | 5/1987 | Wareing | 548/342 |
| 4,898,955 | 2/1990 | Van Koten et al. | 556/12 |
| 5,169,862 | 12/1992 | Burke et al. | 514/450 |

OTHER PUBLICATIONS

Kamienski et al., *J. Org. Chem.*, 30, pp. 3498–3504 (1965).

*Primary Examiner*—Edward A. Miller
*Attorney, Agent, or Firm*—Charles C. Fellows; Robert L. Andersen

[57] ABSTRACT

An ether-free organolithium-lithium organoamide composition represented by the formula $$Li_xR^1{}_a(NR^3R^4)_b$$

wherein $R^1$, $R^3$ and $R^4$ are independently selected from the group of primary, secondary and tertiary alkyl groups containing 2 to 20 carbon atoms, cycloalkyl groups containing 3 to 20 carbon atoms and aryl groups containing 6 to 10 carbon atoms and wherein $R^3$ and $R^4$ may also be hydrogen and a hydrocarbon solvent with the proviso that at least one of $R^3$ and $R^4$ is other than hydrogen.

2 Claims, No Drawings

ETHER FREE ORGANOMETALLIC AMIDE COMPOSITIONS

This application is a division of pending U.S. application No. 496,556 filed Mar. 19, 1990, now abandoned, which was a division of U.S. application No. 160,229 filed Feb. 25, 1988, now U.S. Pat. No. 4,944,894, and a CIP of U.S. application No. 025,412 filed Mar. 13, 1987, now abandoned.

This invention concerns novel ether free organometallic amides and a process for their manufacture.

Organometallics have long been used in the preparation of pharmaceutical, agricultural and specialty chemicals. Metal amides have been frequently used to metallate a substrate as the nitrogen metal bond will react to replace an active hydrogen on a substrate and release the corresponding amine.

Organoamides of magnesium are useful metallating agents in chemical reactions. C. R. Hauser, H. G. Walker and F. C. Frastick, Jr., in J. Am. Chem. Soc. 69 295 (1947) and J. Am. Chem. Soc. 71 1360 (1949) reported use of bromomagnesiumdiethylamide and magnesium diisopropylamide to promote self-condensation of certain esters in diethyl ether. G. Bradley et al., in Eur. J. Med Chem 15 375 (1980) suggest that the so-called "Hauser Base" bromomagnesium diisopropylamide be considered as an alternative for lithium diisopropylamide in many of its numerous applications. The Hauser Base was prepared according to the Bradley et al., procedure and the product was a slurry. While slurries can easily be utilized when prepared in-house, hydrocarbon solutions rather than slurries are preferred commercial products for ease of use and wide acceptability.

Preparation of magnesium bisdialkylamides from kylmagnesium compounds and dialkylamines in tetrahydrofuran and other ethers is known (see Ashby, Lin and Goel, J. Org. Chem. Vol. 43, No. 8 pp 1564–1568, 1978). However, the users of magnesium bisdialkylamides compounds often desire ether free hydrocarbon solutions of the amides. Unfortunately, ethers are known to be quite difficult to separate from the lower dialkylmagnesium compounds and the downstream amides (see Concerning The Purity of Magnesium and Beryllium Alkyls and Halides Prepared By Different Methods by E. C. Ashley and R. C. Arnott J. Organometal. Chem. 14 (1968) 1–11 and Joh and Kataki in Macromolecular Vol. 3, No. 3, May–June, 1970 report separating dioxane from a dialkylmagnesium.)

Hydrocarbon-soluble organometallic complexes of metals of Groups I and IIA of the periodic table are disclosed by C. W. Kamienski and J. F. Eastman in U.S. Pat. No. 3,742,077 and its divisional U.S. Pat. Nos. 3,822,219 and 3,847,883. Their means to achieving hydrocarbon solubility requires that at least one of the organometallic compounds involved be hydrocarbon-soluble while the other component may be hydrocarbon insoluble. Solubility does not occur when two insoluble components such as ethyllithium and diethylmagnesium are simply mixed together; the corresponding insoluble methyl compounds are even excluded from the scope of the invention.

There is a need for hydrocarbon soluble as well as insoluble ether free organometallic amides for use in organic synthesis; for example in preparation of alcohols from non-enolizable ketones and aldehydes. Ether free dialkylmagnesium compounds are known to react more efficiently with substrates in metallation reactions (University Microfilms, Ann Arbor, Mich., Order No. 68-9810 page 60). Since magnesium bisorganoamides are less nucleophilic than dialkylmagnesium but still strongly basic they have greater utility in metallation reactions. In cases where the divalency of the cation is important, magnesium metallating agents are needed for improved performance over monovalent lithium. Moreover, lithium diisopropylamide is known to have only limited solubility in hydrocarbons; for example only 0.2 normal in heptane (C. W. Kamienski and D. H. Lewis, J. Org. Chem. Vol. 30, p 3498, 1965). Whereas, the ether free magnesium bis(diisopropyl)amide of this invention has been found to be soluble to the extent of 1.4 normal in heptane.

The present invention provides novel, ether free, magnesium bisorganoamides and lithium-magnesiumorganoamides, a method of preparing them and bimetallic organoamides. The general method reacts two equivalents of an amine with a dialkylmagnesium compound in a liquid hydrocarbon solvent medium. The dialkylmagnesium compound must be ether free. Although at least one ether free dialkylmagnesium compound, a dibutylmagnesium compound (DBM) containing n-butyl- and s-butyl groups is commercially available, others can be produced in liquid hydrocarbon solvents and reacted with various amines such as dialkylamines, heterocyclic amines and so forth to produce magnesium bisorganoamides and other magnesium organoamides which are ether free. This is conveniently done in a liquid hydrocarbon solvent by reacting magnesium, preferably activated magnesium, with a suitable alkyl halide and reacting the resulting reaction product with an amine such as a dialkylamine to produce the desired magnesium bisdialkylamide (MDA). Generally reaction temperatures do not exceed about 100° C. or the solvent reflux temperature.

There are several process variations which can be employed to effect production of the desired magnesium bisdialkylamide compounds. These variations will be explained using as exemplary reactants n-butylchloride, n-butyllithium, diisopropylamine and activated magnesium. Those skilled in the art will recognize that other reactants can be employed in place of those listed here only for exemplary or explanatory purposes.

In accordance with one variation of the method of the present invention, two moles of n-butylchloride and two moles of activated magnesium are reacted in a liquid hydrocarbon solvent having a boiling point equal to or less than 100° C. to produce a di-n-butylmagnesium plus magnesium chloride product which may be a complex, and which precipitates. In the second step the di-n-butylmagnesium-magnesium chloride complex is reacted with two moles of diisopropylamine (DIPA) to yield two moles of chloromagnesium amide plus two moles of butane which leaves as a gas; this solid product may be a complex of magnesium bisdiisopropylamide and magnesium chloride. Chloromagnesium amide complex as a solid is also prepared in one step reaction by reacting activated magnesium metal with one mole of n-butyl chloride and one mole of diisopropylamine in hydrocarbon solvents such as hexane, cyclohexane, or heptane. The chloromagnesium amide or the complex product of the previous step is reacted with normal n-butyllithium to produce soluble n-butylmagnesiumamide plus solid lithium chloride. The major reaction product is a magnesium bisdiisopropylamide complexed with di-n-butylmagnesium. This product is also identified as n-butylmagnesium diisopropylamide (n-BuMg-N(iPr)₂); in the next step this reaction product is reacted with additional diisopropylamine to produce the magnesium bisdiisopropylamide product plus butane. This product is soluble so the lithium chloride can be removed by filtration. Should a lower boiling hydrocarbon be desired in the process, then diisopropylamine is advantageously added at the same time as the n-butylchloride in step 1 to lower the reaction temperature. It is thought that the diisopropylamine acts as a Lewis base in this reaction as well as a reactant. In like manner, diisopropylamine and n-butyllithium can also be added simultaneously to the chloromagnesium(organo)amide in step 3 to form magnesium bisdiisopropylamide.

A second process variation in accordance with this invention reacts two moles of n-butylchloride with two moles of magnesium to produce di-n-butylmagnesium plus magnesium chloride both of which are precipitated products (known in the art). The reaction product from step 1 is reacted with two moles of n-butyllithium to produce two moles of di-n-butylmagnesium plus two moles of lithium chloride which precipitates (known in the art). The reaction product of the second step, di-n-butylmagnesium plus lithium chloride, is reacted with two moles of diisopropylamine to produce magnesium bisdiisopropylamide plus butane; the lithium chloride, which is a solid, may be removed from this hydrocarbon soluble product. As was done in method 1, if desired, the diisopropylamine can be added simultaneously with n-butyllithium in step 2.

A third process variation in accordance with this invention reacts a mole of n-butylchloride and ethylchloride or n-hexylchloride or n-octylchloride with two moles of magnesium to produce a hydrocarbon soluble mixed dialkylmagnesium plus magnesium chloride which precipitates (known in the art). Magnesium chloride is filtered off after which the mixed dialkylmagnesium is reacted with two moles of diisopropylamine to form the desired magnesium bisdiisopropylamide plus two moles of a mixed alkane. It is possible to leave the magnesium chloride in the reaction medium during the reaction with diisopropylamine but as in process variation 1, insoluble chloromagnesiumamide is formed which requires extra steps for conversion to magnesium bisdiisopropylamide.

A fourth process variation in accordance with this invention reacts two moles of n-butylchloride with two moles of magnesium to produce a mole of di-n-butylmagnesium plus magnesium chloride which precipitate as solids (known in the art). The second step of this variation reacts the di-n-butylmagnesium and magnesium chloride with two moles of secondary butyllithium to produce two moles of hydrocarbon soluble n-butyl, s-butylmagnesium plus two moles of lithium chloride which precipitates and can be removed by filtration (known in the art). The n-butyl-s-butylmagnesium is then reacted with two moles of diisopropylamine to form magnesium bisdiisopropylamide plus two moles of butane. On reaction of the n-butyl-sec-butyl magnesium with only one mole of the amine, a hydrocarbon soluble composition (represented by RMgN(iPr)₂) is formed. Other commercially available dialkylmagnesium compounds, such as nbutylethylmagnesium (BEM) and n-butyloctylmagnesium (BOMAG ™) may be substituted for the n-butyl-sec-butylmagnesium.

The various illustrated processes are not restricted to producing hydrocarbon-soluble magnesium bis(secondary amides) but can also be applied successfully to production of other insoluble analogs. Included among such insoluble secondary magnesium amide compounds are for example magnesiumbis(diethyl)amide, magnesium bispyrrollidide. Also contemplated are insoluble primary magnesium bisalkylamides such as magnesium bis(isopropyl))amide, magnesium bis(2-ethylhexyl)amide and magnesium bis-(2,2-dimethyl-1-propyl)amide. Also contemplated are intermediates in the above process of manufacturing the magnesium bis(organo)amides, such as, e.g., halomagnesium(organo)amides, particularly chloromagnesium diisopropyl amide, and also alkylmagnesium(organo)amides such as, e.g., n-butylmagnesium diisopropylamide and sec-butylmagnesium(organo)amides.

The reaction of a diorganomagnesium compound with a diorganoamine in accordance with the present invention can be represented by the reaction equation

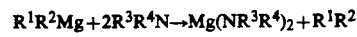

wherein $R^1$, $R^2$, $R^3$ and $R^4$ are independently selected from hydrogen, primary, secondary and tertiary alkyl and cycloalkyl groups containing 2 to 20 carbon atoms and aryl groups containing 6 to 10 carbon atoms. When less than two moles of amine are used per mole of diorganomagnesium compound the alkylmagnesium organoamide produced can be represented by the formula

wherein $R^1$, $R^3$ and $R^4$ have the meanings hereinbefore ascribed to them and x is equal to or greater than 0.1 and less than 2. These latter compounds, alkylmagnesium organoamides such as n-butylmagnesium diisopropylamide, s-butylmagnesium diisopropylamide and so forth are known to be useful in the manufacture of catalysts used in the polymerization of rubber.

The first process variation discussed above involves reaction of diisopropylamine in two stages whereas process variations 2, 3 and 4 involve only single additions of diisopropylamine. Process 3, however, can also be operated like process 1 if the magnesium chloride is not filtered off in step 1. Then additional steps are necessary in order to convert the insoluble complex (chloromagnesiumamide) through further reactions with either normal or secondary butyllithium to form an alkylmagnesium dialkylamide followed by reaction with additional diisopropylamine to form the desired magnesium bisdiisopropylamide.

It is known that alkali metal organoamides, such as lithium diisopropylamide (LDA) are insoluble of themselves in purely hydrocarbon solvents at ordinary temperatures. It has now surprisingly been found that hydrocarbon-insoluble LDA can be made soluble in ether-free hydrocarbon solutions by the addition of magnesium bisdiisopropylamide, even in those cases where the lithium to magnesium ratio is significantly greater than one.

This aspect of the invention concerns bimetallic amide compositions, termed here lithium magnesium diorganoamides, which may be represented by the formula

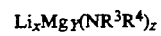

wherein R3 and R4 have the meaning ascribed to them herein above, $x+y=1$ and $z=x+2y$. In specific examples, the compounds $Li_{0.01}Mg_{0.99}(NR^3R^4)_{1.99}$ and Li$_{0.99}$Mg$^{0.01}$(NR$^3$R$^4$)$^{1.01}$ represent opposite ends of the mole fraction range for Li and Mg. The maximum value for z is thus 2.0 and the minimum value for z is 1.0, and these values occur only when the pure compounds Mg(NR$^3$R$^4$)2 and LiNR3R4, respectively, would be present. Compositions with high lithium levels are useful as metallating agents and compositions high in magnesium are useful as alkylating agents. These bimetallic organoamides are usefully dissolved in the same liquid hydrocarbon solvents as the magnesium bisorganoamides of this invention.

A Li$_{0.9}$Mg$_{0.1}$(N(iPr)$_2$)$_{1.1}$ product was found to be soluble in pure cyclohexane to the extent of an overall amide (N(iPr)2) concentration of 1.43 moles per liter at ordinary temperatures. It was found that variation of the Li/Mg ratio in these mixed diisopropylamides between 0.1-10 did not improve the solubility beyond the level of about 1.5 moles of amide/liter, which product solutions were not stable to precipitation for longer than a few days at ambient or room temperatures.

Magnesium bisdiisopropylamide/lithium diisopropylamide mixtures are soluble up to about 90% lithium diisopropylamide with 10% added magnesium bis-diisopropylamide, but the maximum solubility does not exceed the total amide solubility of about 1.4 to 1.5 moles per liter. Interestingly, lithium diisopropylamide's solubility is maintained in the presence of magnesium bisdiisopropylamide in such hydrocarbon solvents in the absence of ethers for limited periods of time, even at cold temperatures.

Such hydrocarbon-soluble bimetallic lithium magnesium diisopropylamides are readily prepared by slow addition (with cooling) of an alkyllithium compound, such as n-butyllithium, dissolved in a hydrocarbon solvent such as cyclohexane, to a solution of magnesium bisdiisopropylamide in cyclohexane, containing diisopropylamine in a quantity equivalent to the n-butyllithium being added.

When a lesser quantity of an organoamine is present in the above mixture than is necessary to react with all of the alkyllithium being added, then hydrocarbonsoluble ether-free organosubstituted lithium magnesiumorganoamides are produced which can be represented by the formula $$Li_xMg_yR^1{}_a(NR^3R^4)_b$$

wherein R$^1$, R$^3$ and R$^4$ have the meaning ascribed to them herein above, x+y=1 and a+b=x+2y.

These compositions can also be formed by direct admixture of an alkyllithium and magnesium bisorganoamide or admixture of a dialkylmagnesium and lithium organoamide.

Surprisingly, it has also been discovered that, even in the absence of any magnesium diorganoamide (y=zero in above formula), reaction of alkyllithium with less than a stoichiometric amount of diorganoamine leads to the formation of hydrocarbon soluble organolithium/lithium organoamide compositions represented by the formula $$(LiR^1)_x \cdot (Li(NR^3R^4))_y \text{ or, as above, } Li_xR^1{}_a(NR^3R^4)_b$$

wherein R$^1$, R$^3$ and R$^4$ have the meaning ascribed to them herein above, and a+b=x. These compositions have been found to be quite stable relative to ether-containing solutions of lithium organoamides.

The products of this invention are prepared from numerous different amine types of the formula $$R_xNH_y$$

and includes the following depending on the values assigned to x and y:

1. Amine types where x=2 and y=1 — These are C$_2$-C$^{20}$ dialkylamines (secondary amines) such as dimethylamine, diethylamine, di-n-propylamine, diisopropylamine, di-n-hexylamine, dicyclohexylamine, and isopropylcyclohexylamine, diphenylamine, phenylisopropylamine, and phenyl-n-butylamine.

2. Amine types where x=1 and y=1 — These are cycloalkyleneimines (secondary amines) such as tetramethyleneimine, common name=pyrrollidine; pentamethyleneimine, common name=piperidine; and the like in which the R group is a diradical; that is, possesses two points of attachment to nitrogen. Included among such R groups are those cycloalkylene radicals possessing a hetero atom, either in the chain itself such as for example the ethyleneoxyethyl diradical (common name for this amine is morpholine), or as part of a radical attached to the cycloalkylene moiety such as the 2-methoxytetramethylene diradical (common name for this amine is 2-methoxypyrrollidine). Included in this type are lower alkyl disubstituted compounds such as 2,5-dimethylpyrrolidine, 2,6-dimethylpiperidine and the like.

3. Amine types where x=1 and y=2 — These are monoalkylamines (primary amines) such as methylamine, ethylamine, n-propylamine, 2-ethylhexylamine, and isopropylamine, aniline, and toluidine.

The products made from lower dialkylamines tend to be hydrocarbon insoluble but it was found that amines containing secondary alkyl groups such as diisopropylamine are hydrocarbon soluble. Similarly the C$_5$ and C$_6$ cyclic amines are hydrocarbon insoluble but products of the invention made from lower alkyl substituted cyclicamines such as 2,2,6,6-tetramethylpiperidine and 2,6dimethylpiperidine are hydrocarbon soluble. Products made from longer straight chain amines such as di-n-hexylamine tend to be soluble but surprisingly products made from dicyclohexylamine are not soluble in hydrocarbon solvents.

The magnesium metal, when used in this method, is preferably activated by heating the metal at the atmospheric reflux temperature of the hydrocarbon selected as the reaction medium in the presence of a small amount of iodine for about 60 minutes in an inert atmosphere. This and other magnesium activation techniques are well known in the art. The amount of iodine employed and treatment time and temperature can vary a great deal. The magnesium can be in any form but to facilitate the reaction with the alkyl halide they are preferably used in powder or chip form.

The alkyl halide used to react with magnesium metal is selected from C$_1$ to C$_{20}$ alkyl halides in which the halide is bromine, chlorine or iodine. The C$_1$ to C$_8$ alkyl halides are preferred and C$_1$ to C$_4$ alkyl halides are most preferred because in the process the alkyl group is removed as an alkane and the gaseous alkanes are easiest to remove from the reaction medium.

The inert liquid hydrocarbon solvent employed in the method of the invention can be selected from many inert liquid hydrocarbon solvents such as n-hexane, cyclohexane, n-heptane, methylcyclohexane, isoparafinic solvents such as Isopar TM E, G or H with n-heptane and cyclohexane being preferred. Aromatic solvents may also be employed, for example toluene or xylene.

The organolithium used in the method of the invention is selected from $C_1$ to $C_{20}$ preferably $C_1$ to $C_8$ alkyl-, cycloalkyl- and aryllithium compounds and most preferably from n-butyllithium, s-butyllithium and t-butyllithium.

The following examples further illustrate the invention. All examples using lithium and/or magnesium metals were conducted under an argon atmosphere.

EXAMPLE 1: SYNTHESIS OF A SOLUBLE N-BUTYLLITHIUM/LITHIUM DIISOPROPYLAMIDE COMPOSITION (50/50 MOLE %) IN CYCLOHEXANE (NO LEWIS BASE)

This experiment shows that a highly soluble, Lewis base free composition of n-butyllithium/lithium diisopropylamine composition (50/50 mole %) which is more thermally stable than LDA solutions in THF can be synthesized.

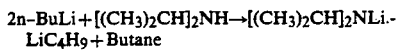

A 100 ml bottle was dried in an oven (150° C.), purged with argon and then equipped with a rubber septum. Next, n-butyllithium (0.098 mole) in cyclohexane was added to the bottle via syringe. Dry diisopropylamine (0.49 mole) was then added dropwise, also by syringe, over a period of 10 minutes. The bottle and contents became warm (40° C.) due to the formation of lithium diisopropylamide and butane. The product solution was cooled to about 25° C. The final product (W.E. titration=1.70M) was slightly yellow, clear and contained no solids indicating the n-BuLi/LDA complex to be quite soluble. This composition was determined to be non-pyrophoric as compared to 16 weight % n-butyllithium in cyclohexane. The product solution was placed in the refrigerator (3±3° C.) and after five days precipitation occurred (white crystals). These crystals redissolved on warming. ELC analyses indicated the product to be a 50/50 mole % composition of n-butyllithium/lithium diisopropylamide.

COMPARATIVE EXAMPLE 1: SYNTHESIS OF LITHIUM DIISOPROPYLAMIDE IN CYCLOHEXANE (NO LEWIS BASE)

Example 30 was repeated except that n-butyllithium (0.037 mole) in cyclohexane was reacted with diisopropylamine (0.037 mole). The final lithium diisopropylamide product contained solids and was very, very viscous like a glass.

EXAMPLE 2: SYNTHESIS OF A SOLUBLE N-BUTYLLITHIUM/LITHIUM DIISOPROPYLAMIDE COMPOSITION (50/50 MOLE %) IN CYCLOHEXANE (NO LEWIS BASE)

Example 1 was repeated except that n-butyllithium (0.036 mole) in cyclohexane was employed to react with diisopropylamine (0.18 mole). The resultant 1:1 n-butyllithium/lithium diisopropylamide complex product solution was completely soluble in cyclohexane (W.E. titration=1.31N), contained no precipitate, and was non-viscous. After 42 days in the refrigerator (3±3° C.) this product solution remained clear (no precipitation).

EXAMPLE 3: SYNTHESIS OF A SOLUBLE N-BUTYLLITHIUM/LITHIUM DIISOPROPYLAMIDE COMPOSITION (33/67 MOLE %) IN CYCLOHEXANE (NO LEWIS BASE)

Example 1 was repeated except that n-butyllithium (0.037 mole) in cyclohexane was reacted with diisopropylamine (0.025 mole). The resultant 1:2 n-butyllithium/lithium diisopropylamide complex was completely soluble in cyclohexane (W.E. titration=1.33M) and contained no precipitation. The final product was slightly viscous. After 21 days in the refrigerator (3±3° C.) the product solution contained no precipitation.

What is claimed is:

1. An ether free, hydrocarbon soluble, thermally stable, low viscosity organolithium-lithium organoamide composition consisting of ingredients represented by the formula

wherein $R^1$, $R^3$ and $R^4$ are independently selected from the group consisting of primary, secondary and tertiary alkyl groups containing 2 to 8 carbon atoms, cycloalkyl groups containing 3 to 8 carbon atoms and aryl groups containing 6 to 10 carbon atoms, the mole ratio of x to y varies from 1 to 1 to 1 to 2.03, in a hydrocarbon solvent.

2. The ether free composition of claim 1 wherein $R^1$ is butyl and $R^3$ and $R^4$ are each isopropyl.

* * * * *